(12) United States Patent
Gao et al.

(10) Patent No.: US 8,389,243 B2
(45) Date of Patent: Mar. 5, 2013

(54) METHODS OF SPRAYING SACCHARIFICATION ENZYMES AND FERMENTATION ORGANISMS ONTO LIGNOCELLULOSIC BIOMASS FOR HYDROLYSIS AND FERMENTATION PROCESSES

(75) Inventors: Johnway Gao, Federal Way, WA (US); Benjamin Levie, Mercer Island, WA (US); Dwight Anderson, Puyallup, WA (US)

(73) Assignee: Catchlight Energy LLC, Federal Way, WA (US)

( * ) Notice: Subject to any disclaimer, the term of this patent is extended or adjusted under 35 U.S.C. 154(b) by 295 days.

(21) Appl. No.: 12/816,999

(22) Filed: Jun. 16, 2010

(65) Prior Publication Data
US 2011/0312033 A1 Dec. 22, 2011

(51) Int. Cl.
*C12P 19/00* (2006.01)
*C12P 1/02* (2006.01)

(52) U.S. Cl. ......... 435/72; 435/162; 435/163; 435/164; 435/165; 435/170; 435/171; 435/209

(58) Field of Classification Search .................. 435/72, 435/171, 204, 161, 162, 163, 164, 165
See application file for complete search history.

(56) References Cited

U.S. PATENT DOCUMENTS

| | | | |
|---|---|---|---|
| 6,924,133 B1 | 8/2005 | Jorgensen et al. | |
| 2007/0031918 A1* | 2/2007 | Dunson et al. | 435/41 |
| 2009/0053770 A1* | 2/2009 | Hennessey et al. | 435/72 |
| 2010/0124770 A1* | 5/2010 | Sabesan et al. | 435/101 |
| 2010/0129909 A1* | 5/2010 | Stuart | 435/375 |
| 2010/0159552 A1* | 6/2010 | Benson et al. | 435/165 |
| 2010/0203605 A1* | 8/2010 | Kim et al. | 435/161 |
| 2010/0304455 A1* | 12/2010 | Inoue et al. | 435/165 |

FOREIGN PATENT DOCUMENTS

| JP | 09268201 A | * 10/1997 |
|---|---|---|
| JP | 2002045830 A | * 2/2002 |
| WO | WO 2008047679 A1 | * 4/2008 |

OTHER PUBLICATIONS

Merriam-Webster online dictionary definition of impregnated www.maeriam-webster.com/impregnated downloaded Jun. 12, 2012.*
Aden, Andy, "Biochemical Production of Ethanol from Corn Stover: 2007 State of Technology Model", National Renewable Energy Laboratory, Technical Report NREL/TP-510-43205, May 2008, 15 pages.
Dasari et al., "The Effect of Particle Size on Hydrolysis Reaction Rates and Rheological Properties in Cellulosic Slurries", Applied Biochemistry and Biotechnology, vol. 136-140, 2007, pp. 289-299.
Galbe et al., "A review of the production of ethanol from softwood", Applied Microbiology and Biotechnology, vol. 59, 2002, pp. 618-628.
Helle et al., "Optimization of spent sulfite liquor fermentation", Enzyme and Microbial Technology, vol. 42, 2008, pp. 259-264.
Jorgensen et al., "Liquefaction of Lignocellulose at High-Solids Concentrations", Biotechnology and Bioengineering, vol. 96, No. 5, Apr. 1, 2007, pp. 862-870.
Kristensen et al., "Yield-determining factors in high-solids enzymatic hydrolysis of lignocellulose", Biotechnology for Biofuels, vol. 2, 2009, 10 pages.
Yan et al., "Dilute sulfuric acid cycle spray flow-through pretreatment of corn stover for enhancement of sugar recovery", Bioresource Technology, vol. 100, 2009, pp. 1803-1808.
Zacchi et al., "Economic evaluation of preconcentration in production of ethanol from dilute sugar solutions", Biotechnology and Bioengineering, vol. 34, No. 2, Jun. 1989, pp. 223-233.
Zhu et al., "Ethanol production from SPORL-pretreated lodgepole pine: preliminary evaluation of mass balance and process energy efficiency", Applied Microbiology and Biotechnology, vol. 86, No. 5, 2010, pp. 1355-1365.

* cited by examiner

Primary Examiner — Susan Hanley
(74) Attorney, Agent, or Firm — Morrison & Foerster LLP (57) ABSTRACT

The present invention provides spray methods of delivering saccharification enzymes, fermentation organisms, and other hydrolysis or fermentation ingredients onto lignocellulosic biomass. The methods reduce the need for mechanical mixing when the biomass solids are undergoing enzymatic hydrolysis, and reduce dilution to allow higher product titers in the hydrolysis and/or fermentation steps.

18 Claims, 7 Drawing Sheets

METHODS OF SPRAYING SACCHARIFICATION ENZYMES AND FERMENTATION ORGANISMS ONTO LIGNOCELLULOSIC BIOMASS FOR HYDROLYSIS AND FERMENTATION PROCESSES

BACKGROUND

1. Field

The present disclosure relates generally to spray methods for delivering saccharification enzymes and fermentation organisms onto lignocellulosic biomass. More specifically it relates to spray methods using a pretreatment prehydrolysate as the delivery liquid in hydrolysis or simultaneous hydrolysis and fermentation processes, thereby reducing the amount of dilution and the need to mix the saccharification or fermentation reaction mixture, while increasing the titer of a saccharification and/or fermentation product.

2. Related Art

In the hydrolysis and fermentation of cellulosic biomass to ethanol or other biofuels and bioproducts, the titer of the final product is lower than starch based fermentation, and therefore requires more energy for distillation. A minimum solids loading of 10% going into hydrolysis has been suggested as having an acceptable level of distillation energy requirements. M. Galbe & G. Zacchi, *A review of the production of ethanol from softwood*, Applied Microbiology and Biotechnology 59, 618-628 (2002).

Increasing final product titer may be achieved with higher solids loadings, but handling high solids introduces mixing requirements that increase the complexity and energy cost of the process. Mixing power requirements increase with increasing solids loadings, so non-conventional mixing techniques have been applied to biomass reactions at high solids concentration. For example, a free-fall mixer has been applied to wheat straw loadings of up to 40% solids. Henning Jorgensen, et al., *Liquifaction of lignocelluloses at high solids concentrations*, Biotechnology and Bioengineering 96, 862-870 (2006). Mixing may be accomplished in a number of other ways, including high consistency mixers, screw presses, static mixers, or by spray application. One example of spray application of acid is Yan et al. L. Yan, et al., *Dilute sulfuric acid cycle spray flow-through pretreatment of corn stover for enhancement of sugar recovery*, Bioresource Technology 100, 1803-1808 (2009). High solids may also slow hydrolysis in the reactor for reasons other than mixing limitations. Jan B. Kristensen, et al., *Yield-determining factors in high solids enzymatic hydrolysis of lignocellulose*, Biotechnology for Biofuels 2, 11 (2009).

Product titer may also be increased by reducing dilution steps in hydrolysis and fermentation processes. Methods of lignocellulose hydrolysis and/or fermentation include separate hydrolysis and fermentation (SHF—hydrolysis first, then fermentation) or simultaneous saccharification and fermentation of lignocelluloses (SSF—hydrolysis and fermentation happens at the same time). Saccharification and fermentation of lignocellulosic biomass typically require an acidic and/or a chemical pretreatment process or an alkaline chemical pretreatment process. In a biomass pretreatment process without complete biomass hydrolysis, a pretreated biomass solids stream and a prehydrolysate stream are generated. The pretreated biomass stream (solids fraction) is rich in cellulose while the prehydrolysate stream (liquid fraction) is rich in hemicellulose sugars or hemicellulose oligomers, along with lignin, extractives, furans, aldehydes, acetic acid, or other inhibitors that restrict the growth and productivity of a fermenting organism. Additionally, the prehydrolysate stream usually has a pH outside of the typical enzymatic hydrolysis pH range (4.8 to 6.5) or typical fermentation pH range (3.5 to 7.5). Similarly, the pretreated biomass solids also may also contain inhibitors and a different pH from the enzymatic hydrolysis pH and the fermentation pH. Therefore, prehydrolysate and pretreated biomass conditioning are often needed before an enzymatic hydrolysis and a fermentation process.

The prehydrolysate is typically separated from the solids after pretreatment and conditioned by overliming (Andy Aden, *Biochemical Production of Ethanol from Corn Stover: 2007 State of Technology Model*, NREL/TP-510-43205 (2008)) or ion exchange (J. Y. Zhu, et al., *Ethanol production from SPORL-pretreated lodgepole pine: preliminary evaluation of mass balance and process energy efficiency*, Applied Microbiology and Biotechnology 86, 1355-1365 (2010)) and fermented separately from the solids fraction. In these scenarios, it is necessary to add dilution to accomplish pH changes, enzyme loading, and, in the case of simultaneous saccharification and fermentation (SSF), fermentation organism loading.

The solids fraction of the pretreatment process is typically washed to remove fermentation inhibitors, then hydrolyzed, and fermented either separately or together with the prehydrolysate. Since both the prehydrolysate and the hydrolysate contain sugars that could be fermented to maximize yield, any water added up to the point of fermentation reduces the ultimate product titer. This requires greater energy requirements for separation with distillation. The high initial viscosity and associated poor mixing properties of the solids fraction of the pretreated cellulosic biomass may also reduce the product titer. For lab scale experimentation, pretreated cellulose is often hydrolyzed at 5% solids or even lower to enable mixing, and mixing effectiveness decreases (or requires more power) as solids increase. The difference between 10% solids and 20% solids going into hydrolysis, for example, is a factor of two on the ultimate product titer, resulting in approximately a factor of two in distillation energy use. G. Zacchi & A. Axelsson, *Economic evaluation of preconcentration in production of ethanol from dilute sugar solutions*, Biotechnology and Bioengineering 34, 223-233 (1989). Greater hydrolysis reactor volume, fermentor volume and distillation column volume will be required for lower product titer liquid handling, potentially tripling the total capital cost of downstream processing.

In both SHF and SSF, it has been anticipated that "to increase the sugar concentration in a future large-scale operation, it is assumed that the whole slurry after pretreatment would be used without introducing separation steps that would dilute the process stream." M. Galbe & G. Zacchi, Applied Microbiology and Biotechnology 59, 618-628 (2002). Therefore, what is needed is a method of hydrolyzing and fermenting biomass compositions to produce product liquids of high titer with minimal dilution steps. The method would make use of the prehydrolysate to the extent needed to optimize mixing, enzymatic hydrolysis, and fermentation. The prehydrolysate stream may be used to accomplish pH changes, enzyme loading, and, in the case of SSF, fermentation organism loading to avoid adding dilution water.

SUMMARY

The present invention provides spray methods of delivering saccharification enzymes, fermentation organisms, and/or other hydrolysis or fermentation ingredients onto solid biomass comprising lignins and/or cellulose. More specifically it relates to spray methods using a pretreatment prehydrolysate as the delivery method for a composition to promote hydrolysis or simultaneous hydrolysis and fermentation processes in solid biomass to be broken down, thereby reducing the amount of dilution and increasing the titer of a saccharification or fermentation product.

In one non-limiting variation, the present invention provides a method of producing a saccharification product from a pretreated biomass composition, the method comprising: a) spraying a liquid comprising one or more saccharification enzymes onto the pretreated biomass composition to form an impregnated biomass composition; and b) maintaining the impregnated biomass composition under suitable conditions to promote hydrolysis of components in the impregnated biomass composition to produce the saccharification product. In some non-limiting variations, the liquid further comprises one or more fermentation organisms, and wherein the one or more fermentation organisms ferment sugars produced by hydrolysis to produce a fermentation product. In some non-limiting variations, the liquid is a prehydrolysate produced from the pretreated biomass composition. In other non-limiting variations, the liquid is a prehydrolysate produced from a second pretreated biomass composition.

In another non-limiting variation, the present invention provides a method of producing a saccharification product from a pretreated biomass composition comprising a prehydrolysate and pretreated biomass solids, the method comprising: a) separating the prehydrolysate from the pretreated biomass solids to form a first prehydrolysate liquid; b) adding one or more saccharification enzymes to the first prehydrolysate liquid to form a second prehydrolysate liquid; c) spraying the second prehydrolysate liquid onto the pretreated biomass solids to form an impregnated biomass composition; and d) maintaining the impregnated biomass composition under suitable conditions to promote enzymatic hydrolysis of the impregnated biomass to produce the saccharification product. In some non-limiting variations, the method further comprises: a) adding one or more fermentation organisms to the saccharification product; and b) maintaining the saccharification product under suitable conditions to promote fermentation of sugars produced by hydrolysis to produce a fermentation product.

In some non-limiting variations, the pretreated biomass solids are not rinsed or conditioned before spraying with the second prehydrolysate. In some non-limiting variations, the methods disclosed herein further comprise adjusting the pH of the first or second prehydrolysate to a pH range of 3.0 to 9.0 prior to the spraying step. In some non-limiting variations, the one or more saccharification enzymes are selected from the group consisting of cellulase, beta-glucosidase, xylanase, other hemicellulases, and mixtures thereof. In some non-limiting variations, the fermentation organisms are selected from the group consisting of yeast, mold, algae, bacteria, and mixtures thereof.

In some non-limiting variations, the methods disclosed herein further comprise mixing the pretreated biomass composition with the second prehydrolysate liquid.

In some non-limiting variations, the pretreated biomass solids are transported on a screw or a belt conveyer during the spraying step to form the impregnated biomass composition. In some variations, the methods disclosed herein further comprise moving the impregnated biomass composition with a belt or screw conveyer into a reactor for the hydrolysis.

In some non-limiting variations, the pretreated biomass composition comprises wood chips, and the wood chips are size reduced prior to pretreatment such that prior to size reduction, 50-100% of the wood chips pass through a +7 mm round hole screen, and after size reduction, 50-100% of the wood chips pass through a +3 mm round hole screen. In some non-limiting variations, the pretreated biomass solids are ground up prior to spraying with the second prehydrolysate liquid.

In some non-limiting variations, the pretreated biomass composition is produced from an acid sulfite or acid bisulfite pretreatment process.

In some non-limiting variations, the pretreated biomass composition is produced from an alkaline sulfite or alkaline bisulfite pretreatment process. In some non-limiting variations, the pretreated biomass composition is produced from a neutral chemical pretreatment process or a pretreatment process using water and no additional chemicals.

In some non-limiting variations, the fermentation product has a titer greater than 4.0%. In some non-limiting variations, the hydrolysis produces a sugar yield of 80-100% of the pretreated biomass composition. In some non-limiting variations, the fermentation converts 60-100% of the sugars to the fermentation product.

The present invention further provides a method of producing a fermentation product from a pretreated biomass composition comprising a prehydrolysate and pretreated biomass solids, the method comprising: a) separating the prehydrolysate from the pretreated biomass solids to form a first prehydrolysate liquid; b) adding one or more saccharification enzymes and one or more fermentation organisms to the first prehydrolysate liquid to form a second prehydrolysate liquid; c) spraying the second prehydrolysate liquid onto the pretreated biomass solids to form an impregnated biomass composition; and d) maintaining the impregnated biomass composition under suitable conditions to promote enzymatic hydrolysis of the impregnated biomass composition and fermentation of the saccharification product to form the fermentation product.

BRIEF DESCRIPTION OF THE DRAWINGS

FIG. 1. Smaller, re-chipped chips result in higher sugar yield compared to larger, screened chips in magnesium bisulfite pretreatment with 2% sulfuric acid on wood.

FIG. 2. Batch simultaneous saccharification and fermentation with *Saccharomyces cerevisiae* D5a on calcium bisulfite pretreated softwood and prehydrolysate from re-chipped wood chips.

FIG. 3. Batch simultaneous saccharification and fermentation with *Saccharomyces cerevisiae* T2 on calcium bisulfite pretreated softwood and prehydrolysate from re-chipped wood chips.

FIG. 4. Batch simultaneous saccharification and fermentation with *Saccharomyces cerevisiae* T2 on calcium bisulfite pretreated softwood and prehydrolysate from re-chipped wood chips. The saccharification enzymes and fermentation organisms were added to the prehydrolysate and spray delivered onto the pretreated wood chips.

FIG. 5. Process flow diagram of spraying enzyme(s), fermenting organism(s), and/or nutrients in a prehydrolysate diluent onto pretreated biomass solids.

FIG. 6. Process flow diagram of spraying enzyme(s), fermenting organism(s), and/or nutrients without a prehydrolysate diluent onto biomass solids.

FIG. 7. Process design of spraying enzymes, fermentation organisms, and/or nutrients onto biomass solids using a conveyor to transport the solids under a spraying apparatus and into a hydrolysis and/or fermentation reactor.

DETAILED DESCRIPTION

The following description sets forth exemplary methods, parameters and the like. It should be recognized, however, that such description is not intended as a limitation on the scope of the present invention but is instead provided as a description of exemplary embodiments. From these, a person of ordinary skill would be able to practice the invention without undue experimentation.

1. Definitions

As used herein, "pretreatment" refers to the thermo-chemical treatment of biomass in order to make cellulose available to downstream hydrolysis and biologically-based conversion processes. Unless indicated otherwise, it does not include further processing steps such as separation of solid and liquid phases of the pretreatment product or rinsing or conditioning of the solid or liquid product phases. Similarly, "pretreated biomass solids" refer to biomass solids that have undergone pretreatment, and unless otherwise indicated, a pretreated biomass solid has not received other treatments or processing.

As used herein, the term "prehydrolysate" refers to the liquid fraction of the pretreatment reaction mixture.

As used herein, the term "hydrolysate" refers to the reaction mixture formed from a prehydrolysate and/or pretreated biomass solids after having undergone enzymatic hydrolysis to at least partially break down oligosaccharides into sugars.

As used herein, "saccharification" refers to the enzymatic hydrolysis of biomass to monomeric and/or oligomeric sugars.

As used herein, "saccharification product" refers to the product generated when a saccharification enzyme catalyzes hydrolysis of biomass, typically pretreated biomass.

As used herein, a "saccharification enzyme" refers to an enzyme that is capable of catalyzing the hydrolysis of biomass to monomeric and/or oligomeric sugars.

As used herein, "inhibitor(s)" or "byproduct(s)" refer to side products other than sugars that may be present in both the prehydrolysate after pretreatment and the hydrolysate after enzymatic hydrolysis. Inhibitors, in particular, are byproducts that are capable of interfering with enzymatic hydrolysis or fermentation.

As used here in "comminution" refers to a method where biomass solids are mechanically resized to small or finer particles with a varied particle size range or distribution. In some non-limiting variations, the biomass solids may be woody trunks or branches resized to small or finer chips with a varied chip size range or distribution. In some non-limiting variations, 50-100% of the biomass solids are able to pass through a +7 mm diameter round hole screen prior to comminution. In other non-limiting variations, 50-100% of the biomass solids are able to pass through a +3 mm diameter round hole screen after comminution and may be referred to "re-chipped" wood chips or biomass solids. In some preferred variations, 50-100% of the "re-chipped" wood chips or biomass solids are able to pass through a +7 mm diameter round hole screen and the remaining 0-50% of the "re-chipped" wood chips or biomass solids are able to pass through a +3 mm diameter round hole screen. In some preferred variations, approximately 20-25% of the "re-chipped" wood chips or biomass solids are able to pass through a +7 mm diameter round hole screen and the remaining 75-80% of the "re-chipped" wood chips or biomass solids are able to pass through a +3 mm round hole screen.

As used herein, "spraying" refers to delivering a composition, typically a liquid or slurry or suspension, as a plurality of drops spread relatively evenly onto a material. As used herein, the term "spraying" also encompasses "sprinkling," where a composition is delivered sparsely and with small scale non-uniformity onto a material. In some non-limiting variations, the spraying may be accomplished with a spraying nozzle, a sprinkling nozzle, or some other mechanism such as a flat plate mounted over a conveyor. In some non-limiting variations, the spraying may deposit a fine and constant mist of the composition onto the material or coarse droplets of the composition onto the material, or a mixture of fine and coarse droplets. In some non-limiting variations, the composition or liquid being applied may or may not include solid material, such as biomass particles or other products generated from biomass pretreatment processes. In some non-limiting variations, the composition may be pressurized in a container with compressed gas or air or with a pump or with a gravity head pressure and may exit the container through a spray nozzle that sprays the mixture onto the other material.

As used herein, when the term "about" modifies a number, the term is defined as "approximately," and the number should be interpreted to cover a range that includes its recited value and the experimental error in obtaining the number.

2. Description of the Invention

The present invention provides spray methods of delivering saccharification enzymes, fermentation organisms, and/or other hydrolysis or fermentation ingredients onto solid biomass including lignins and/or cellulose. More specifically it relates to spray methods using a pretreatment prehydrolysate as the delivery method for a composition to promote hydrolysis or simultaneous hydrolysis and fermentation processes in solid biomass to be broken down, thereby reducing the amount of dilution and increasing the titer of a saccharification or fermentation product.

In cellulosic ethanol or other bioproduct fermentation, high solids loading in biomass hydrolysis is one way to achieve high sugar titer, high product concentration, and high productivity in order to reduce capital cost, operation cost, and energy consumption. Hydrolysis or fermentation at an initial 14% or higher solids loading may encounter initial mass transfer difficulties with enzyme and/or fermentation organism and nutrients, thus slowing down the hydrolysis or fermentation process. The methods disclosed herein involve spraying hydrolysis and/or fermentation ingredients onto pretreated biomass solids, e.g., high solids, fibrous cellulose materials to achieve effective mass transfer and maintain high solids loading. Spray application may be as effective for both SHF and SSF as thorough mixing, and increases efficiency by reducing energy usage and reducing or eliminating the need for physical mixing of the biomass with the ingredients added to promote breaking down the solids. The prehydrolysate delivery method requires no additional water for pretreated biomass washing and thus minimizes water usage and wastewater treatment, yet its overall efficiency for converting biomass such as wood chips into water-soluble sugars and/or ethanol is comparable to conventional mixed SSF or SHF processes.

The methods of the present invention provide a method of producing a saccharification product from a pretreated biomass composition, the method comprising: a) spraying a liquid including one or more saccharification enzymes onto the pretreated biomass composition to form an impregnated biomass composition; and b) providing operating conditions for enzymatic hydrolysis of the impregnated biomass composition to produce a saccharification product that typically includes sugars and/or hemicelluloses that are relatively water soluble. The spraying liquid may be prepared by admixing the one or more saccharification enzymes with a prehydrolysate liquid and may or may not contain suspended particles or solids. The prehydrolysate liquid is a composition produced by pretreatment of biomass, and can be the same prehydrolysate produced in the pretreatment process that produced the pretreated biomass for use in this method or a different prehydrolysate produced from a different pretreated biomass. In some non-limiting variations, the spraying composition further includes one or more fermentation organisms, and the one or more fermentation organisms ferment the saccharification products as they are formed to produce a fermentation product. In these non-limiting variations, the spraying liquid includes both the saccharification enzyme(s) and fermentation organism(s), and the enzymatic hydrolyzing and microbial fermenting may be carried out in one reactor. The spraying composition may further include acid, base or buffer to adjust pH to a suitable range; nutrients to sustain growth of a fermentation microorganism; and/or substances to support or enhance the function of enzymes present to help break down cellulose, hemicelluloses or other components of the pretreated biomass.

The methods of the present invention further provide a method of producing a saccharification product from a pretreated biomass composition including a prehydrolysate and pretreated biomass solids, wherein the method includes: a) separating the prehydrolysate from the pretreated biomass solids to form a first prehydrolysate liquid; b) adding one or more saccharification enzymes to the first prehydrolysate liquid to form a second prehydrolysate liquid; c) spraying the second prehydrolysate liquid onto the pretreated biomass solids to form an impregnated biomass composition, preferably without rinsing or treating the pretreated biomass solids; and d) maintaining the impregnated biomass composition under suitable conditions to promote enzymatic hydrolysis of the impregnated biomass composition to produce the saccharification product. In one non-limiting variation, the method further includes e) adding one or more fermentation organisms to the saccharification product; and f) maintaining the saccharification product under suitable conditions to promote fermentation of sugars produced by hydrolysis to produce a fermentation product. In another non-limiting variation, one or more fermentation organisms are added to the first prehydrolysate liquid in addition to the one or more saccharification enzymes to form the second prehydrolysate liquid, the second prehydrolysate liquid including both the saccharification and fermentation organisms is sprayed onto the pretreated biomass solids, and the one or more fermentation organisms ferment the sugars produced by saccharification to produce a fermentation product, typically as a liquid also. In these non-limiting variations, the enzymatic hydrolyzing and fermenting may be carried out in one reactor and may occur concurrently, or they may be done sequentially by performing the saccharification process and then adding fermentation organisms and any needed additives to promote fermenting of the sugars from the saccharification.

In some non-limiting variations, the methods further include adjusting the pH of the first or second prehydrolysate liquid to a pH range of 3.0 to 9.0 prior to the spraying step.

In some non-limiting variations, the one or more saccharification enzymes include cellulase, beta-glucosidase, xylanase, other hemicellulases, and mixtures thereof. In some non-limiting variations, the fermentation organisms include yeast, mold, algae, bacteria, and mixtures thereof.

In some non-limiting variations, the methods of the invention further include mixing the pretreated biomass composition with the second prehydrolysate composition, typically by spraying or sprinkling the second prehydrolysate liquid onto the pretreated biomass.

In some non-limiting variations, the pretreated biomass solids are transported on a screw conveyer or a belt conveyer during the spraying step to form the impregnated biomass composition. In some non-limiting variations, the methods of the invention further include moving the impregnated biomass composition with a screw or belt conveyer into a reactor for the enzymatically hydrolyzing or the enzymatically hydrolyzing and fermenting steps.

In some non-limiting variations, the methods of the invention further include circulating the impregnated biomass composition inside the reactor. In some preferred variations, a slurry pump, a slow agitator, or a slow impeller circulates the impregnated biomass composition.

In some non-limiting variations, the pretreated biomass composition includes wood chips. In some preferred variations, the wood chips are size reduced prior to pretreatment. In some non-limiting variations, 50-100% of the biomass solids are able to pass through a +7 mm diameter round hole screen prior to comminution and are referred to as "screened" wood chips throughout the disclosure. In other non-limiting variations, 50-100% of the biomass solids are able to pass through a +3 mm diameter round hole screen after comminution and are referred to as "re-chipped" wood chips or "re-chipped" biomass solids throughout the disclosure. In some preferred variations, 50-100% of the "re-chipped" wood chips or biomass solids are able to pass through a +7 mm diameter round hole screen, and the remaining 0-50% of the "re-chipped" wood chips or biomass solids are able to pass through a +3 mm diameter round hole screen. In some preferred variations, approximately 20-25% of the "re-chipped" wood chips or biomass solids are able to pass through a +7 mm diameter round hole screen, and the remaining 75-80% of the "re-chipped" wood chips or biomass solids are able to pass through a +3 mm round hole screen.

In some non-limiting variations, the pretreated biomass composition is produced from an acid sulfite or acid bisulfite pretreatment process. In some preferred variations, the pretreated biomass composition is produced from an alkaline sulfite or alkaline bisulfite pretreatment process. Pretreatments can use alkali metal salts or alkaline earth metal salts of bisulfites or sulfites. In some preferred variations, the pretreated biomass composition is produced from a neutral chemical pretreatment process. Pretreatment reactions were conducted for suitable time periods under suitable conditions to promote the desired process. For example, in some preferred variations, the pretreated biomass composition is produced from a pretreatment process using water and no additional chemicals. In some non-limiting variations, the pretreatment temperature is ramped from a lower temperature of about 50-150° C. to a higher temperature of about 150-250° C. over a first period of time and held at the higher temperature for a second period of time. In some non-limiting variations the lower temperature is about 75° C.-125° C. and the higher temperature is about 170-200° C. In some non-limiting variations the lower temperature is about 80-100° C. and the higher temperature is about 170-190° C. In some non-limiting variations, the first period of time is 5-30 minutes and the second period of time is 10-60 minutes. In some non-limiting variations, the first period of time is 10-20 minutes and the second period of time is 15-25 minutes.

Saccharification reactions were conducted for suitable time periods under suitable conditions to promote the desired process. For example, in some non-limiting variations, the saccharification is carried out at 1-20% solids loading (by weight). In other non-limiting variations, the saccharification is carried out at 2-10% solids loading. In other non-limiting variations, the saccharification is carried out at about 5% solids loading. In some non-limiting variations, the pH of the saccharification reaction is about 2-7. In some non-limiting variations, the pH is about 3-6. In other non-limiting variations, the pH is about 4-5. In some non-limiting variations, the saccharification conditions are maintained for 24-72 hours. In some non-limiting variations, the saccharification conditions are maintained for 36-60 hours. In some non-limiting variations, the saccharification conditions are maintained for about 48 hours. In some non-limiting variations, cellulase, beta-glucosidase, xylanase, other hemicellulases, or mixtures of any combination of enzymes are used in the hydrolysis reactions. In some non-limiting variations 5-25 FPU cellulase is used in the enzymatic hydrolysis. In some non-limiting variations, 10-20 FPU cellulase is used in the enzymatic hydrolysis. In some non-limiting variations, about 16 FPU cellulase is used in the enzymatic hydrolysis. In some non-limiting variations, 10-30 U of beta-glucosidase is used in the enzymatic hydrolysis. In some non-limiting variations, 15-25 U of beta-glucosidase is used in the enzymatic hydrolysis. In some non-limiting variations, about 20 U of beta-glucosidase is used in the enzymatic hydrolysis. In some non-limiting variations, 5-20 U of xylanase is used in the enzymatic hydrolysis. In some non-limiting variations, 10-15 U of xylanase is used in the enzymatic hydrolysis. In some non-limiting variations, about 9-10 U of xylanase is used in the enzymatic hydrolysis. In some non-limiting variations, the saccharification produces a sugar yield of 80-100% of the pretreated biomass composition.

Fermentation reactions were conducted for suitable time periods under suitable conditions to promote the desired process. In some non-limiting variations, saccharification may be carried out first, followed by fermentation (SHF). In other non-limiting variations, saccharification and fermentation reactions may be carried out in the same reactor, by adding both saccharification enzymes and fermentation organisms to the pretreated biomass composition in the reactor, and maintaining the reactor under suitable conditions that promote both saccharification and fermentation (SSF). In some non-limiting variations, the concentration of the fermentation organism is 0.5-5 g/L. In other non-limiting variations, the concentration of the fermentation organism is 1-3 g/L. In other non-limiting variations, the concentration of the fermentation organism is about 2 g/L. In some non-limiting variations, the pH of the fermentation reaction is about 4-7. In some non-limiting variations, the pH of the fermentation reaction is about 6-7. In some non-limiting variations, buffers and nutrients may be added to the fermentation reactions, such as, for example, sodium citrate, peptone, or corn steep liquor.

In some non-limiting variations, the fermentation or SSF conditions are maintained for 24-72 hours. In some non-limiting variations, the fermentation or SSF conditions are maintained for 36-60 hours. In some non-limiting variations, the fermentation or SSF conditions are maintained for about 48 hours. In some non-limiting variations, the fermentation product has a titer greater than 4%. In some non-limiting variations, the fermentation product has a titer of 4-20%. In other non-limiting variations, the fermentation product has a titer of 4-10%. In other non-limiting variations, the fermentation product has a titer of 4-6%. In some non-limiting variations, the fermentation converts 60-100% of sugars to the fermentation product, based on the type of sugars the fermenting organisms are selected to process. In some non-limiting variations, the fermentation converts 80-90% of sugars to the fermentation product.

EXAMPLES

Reagents

Magnesium bisulfite (Sigma Catalog #398233) was purchased as a 30% w/w solution. A calcium bisulfite solution of 4 to 7% was made by purging a sulfur dioxide stream into a calcium oxide solution or slurry in the laboratory. Sulfuric acid (95.8% assay and Catalog #A-300-212) was purchased from Fisher scientific. Sodium Citrate (Sigma Catalog #71498), potassium hydroxide (Sigma Catalog #P5958), and urea (Sigma Catalog #U5128) were purchased from Sigma-Aldrich. These reagents were diluted with deionized water or the prehydrolysate to the appropriate concentration for loading the pre-calculated amount into the reactor. All the reported bisulfite reagents and acid loadings are based on the oven dry (OD) weight of the biomass.

Cellulase (Celluclast, Sigma Catalog #C-2730); beta-glucosidase (Novozymes-188, Sigma Catalog #C-6105); and xylanase (Novozymes NS50030; 500 FXU/g) were used in the enzymatic hydrolysis experiments. The activity of celluclast was found to be approximately 80 FPU/ml as measured in Weyerhaeuser Lab (Seattle, Wash.) and activity of beta-glucosidase was reported to be 250 CBU/g (300 CBU/ml) by the supplier (Novozymes). These enzymes were stored in refrigerator below 4° C.

The yeast strain *Saccharomyces cerevisiae* D5a (ATCC 200062) was obtained from American Type Culture Collection (ATCC, Manassas, Va.) and was used in Example 4. Another yeast strain *Saccharomyces cerevisiae* T2 was obtained from Dr. Sheldon Duff at the University of British Columbia and was used in Example 5.

Example 1

Reduction of Chip Size Prior to Calcium Bisulfite Pretreatment

For woody feedstocks in particular, reducing inhibitors byproducts in a pretreatment process may be achieved by reducing the size of the wood chip to enable less severity of time or temperature. Because a small quantity of inhibitor byproducts is present in the prehydrolysate liquid, the prehydrolysate may not require a separate conditioning process to remove the inhibitors prior to using the prehydrolysate as a diluent for enzymatic hydrolysis.

Wood pretreatment and hydrolysis may be carried out on finely ground wood. Hemicellulose removal during the pretreatment process is known to reduce energy requirements for particle comminution; therefore, comminution of wood particles after pretreatment may be more energy efficient. However, comminution prior to pretreatment may also improve the pretreatment process.

Commercial pine wood chips were obtained from a pulp mill in the southern U.S. These pine wood chips represent the "screened" chips in Table 1 and are representative of the feed to a pulp digester in a commercial pulp and paper operation. A sub-sample of these chips was fractured with a BearCat garden chipper with a ¾" screen to obtain the "re-chipped" fiber distribution shown below in Table 1. For the re-chipped chips, the 3 mm round hole fines were removed to avoid circulation problems in the lab pretreatment reactor.

TABLE 1

Size classifications of pretreated and hydrolyzed chip size distributions.

| Chip Treatment | Size Classification (Percent of Total) | | | |
|---|---|---|---|---|
| | +8 mm thickness | +7 mm round hole | +3 mm round hole | −3 mm round hole |
| Screened | 5.5% | 85.8% | 6.8% | 0.5% |
| Re-chipped | 0.0% | 23.5% | 76.5% | 0.0% |

The chip size distributions shown in Table 1 were pretreated in separate runs of a one cubic foot reactor with a sulfite pretreatment consisting of 12% calcium bisulfite on wood with a two-step temperature schedule: ramp from 90° C. to 160° C. in 15 minutes, hold at 160° C. for 30 minutes, ramp to 180° C. quickly (6 minutes), and hold at 180° C. for 20 minutes. This temperature scheme was determined to be optimal for reducing pretreatment severity and inhibitor production under calcium bisulfite pretreatment Conditions. The solubilization of wood in each case was identical at approximately 23% on dry wood basis. The prehydrolysate was collected, and the pretreated, unwashed solids were ground in an Alpine grinder. The prehydrolysate was then recombined with the ground solids and sodium citrate was added as a buffer at a 50 mmol concentration. The composition was subjected to enzymatic hydrolysis at 5% solids with 16 FPU cellulase/dry gram of pretreated solids and 20 U beta-glucosidase/dry gram of pretreated solids at pH 4.8. After 48 hours, the quantity of hydrolyzed sugars was higher and the quantity of inhibitors was lower for the smaller re-chipped size distribution, as shown in Table 2. In addition, the re-chipped has a higher hydrolysis conversion of sugars than the screened: 88% (re-chipped) and 79% (screened). The total furan inhibitors in the prehydrolysate liquor were also lower for the re-chipped over the screened: 0.61% (re-chipped) and 1.02% (screened).

TABLE 2

Effect of particle size reduction on prehydrolysate composition after pretreatment and on total sugar conversion after 48 hour enzymatic hydrolysis.

|  | Un-pretreated Wood | Re-Chipped (smaller chip size) | Screened (larger chip size) |
|---|---|---|---|
| Prehydrolysate Composition (% as polymer on wood) |  |  |  |
| Glucan | 39.5% | 1.30% | 1.30% |
| Xylan + Galactan + Mannan | 18.67% | 6.36% | 5.70% |
| Arabinan | 1.01% | 0.25% | 0.25% |
| Total Sugars (as polymers) | 59.18% | 7.92% | 7.25% |
| HMF in Liquor |  | 0.24% | 0.30% |
| Furfural in Liquor |  | 0.37% | 0.72% |
| Total Furans |  | 0.61% | 1.02% |
| Total Sugar Conversion (Prehydrolysate + Hydrolysate, % of theoretical except for wood) |  |  |  |
| Glucan |  | 100.5% | 89.7% |
| Xylan + Galactan + Mannan |  | 63.2% | 58.0% |
| Arabinan |  | 70.3% | 69.9% |
| Total Sugars (as polymers) | 59.18% on wood | 88.2% | 79.3% |

Example 2

Reduction of Chip Size Prior to Magnesium Bisulfite Pretreatment

Pretreatment tests with magnesium bisulfite 9.6% (wt % on dry wood basis) and sulfuric acid 2% (wt % on dry wood basis) on re-chipped chips and larger chips were compared for the sugar hydrolysis yields and furan formation. Two different pretreatment temperature schemes were tested: (1) a controlled ramp from 90° C. to 180° C. in 15 minutes and held at 180° C. for 20 minutes; and (2) a slower, controlled from 90° C. to 180° C. in 60 minutes and held at 180° C. for 20 minutes. After the pretreatment, the pretreated and unwashed solids were ground in an Alpine grinder, and enzymatic hydrolysis was conducted in 5% pretreated materials using the same procedure as in Example 1 above. The sugar conversion yields are compared in FIG. 1.

Figure 1:
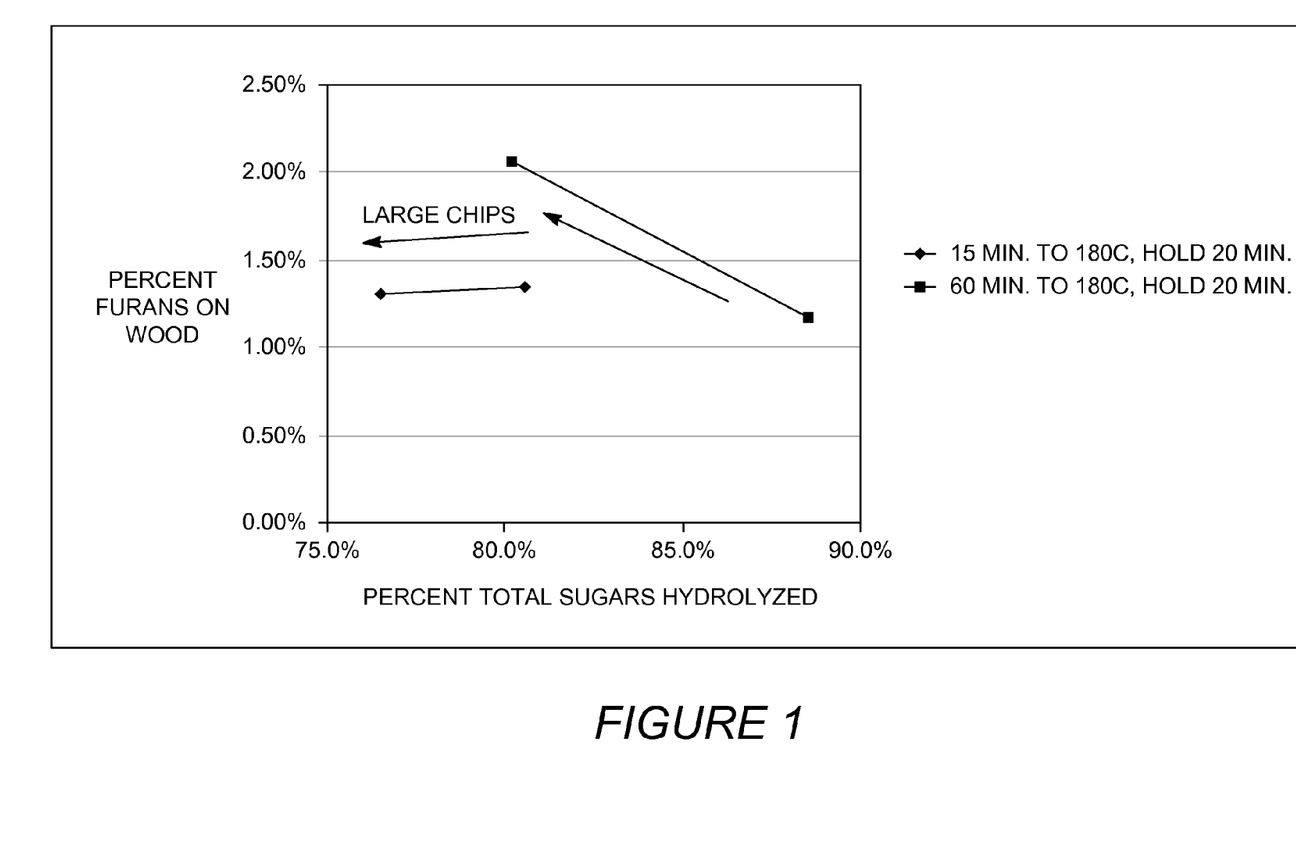

The magnesium bisulfite pretreatment runs produced similar results as was observed for calcium bisulfite in Example 1. Under both temperature schemes, the smaller chips had better hydrolysis characteristics in the one cubic foot reactor. The smaller chip size distribution had a 4% to 8% improvement in total sugar yield upon hydrolysis (FIG. 1). However, the magnesium bisulfite/sulfuric acid runs produced furan concentrations greater than 1% on wood compared to the 0.61% on wood with calcium bisulfite with no exogenous sulfuric acid added (See FIG. 1 and Table 2, smaller chip size). The calcium bisulfite conditions are preferred over the magnesium bisulfite conditions due to lower inhibitor formation and the ability to use the bisulfite reagent without additional acid. Also, the re-chipped chips are preferred over the screened chips due to higher yields of enzymatic hydrolysis. The slower temperature scheme on re-chipped chips significantly reduced furan formation in the cook liquor while the faster temperature ramp scheme showed insignificant impact on furan formation.

Example 3

Spray Application of Enzymes in Prehydrolysate for High Solids Enzymatic Hydrolysis High solids enzymatic hydrolysis was tested on calcium bisulfite pretreated re-chipped chip biomass, using the prehydrolysate as an enzyme delivery vehicle in a spray application. In one single spray application, the enzyme(s) are delivered to the pretreated biomass, the pretreated biomass is neutralized, and mixing of the pretreated biomass and enzymes are achieved. Washing the pretreated biomass with water prior to hydrolysis was not needed. Mechanical agitation and high viscosity mixing were unnecessary for the pretreated biomass hydrolysis.

The re-chipped chips were first pretreated with calcium bisulfite (12 wt % on wood) in the one cubic foot digester in a two-step temperature scheme: ramp from 90° C. to 160° C. in 15 minutes, hold at 160° C. for 30 minutes, ramp from 160° C. to 180° C. in 9.5 minutes, hold at 180° C. for 20 minutes. The prehydrolysate was collected and the pretreated, unwashed solids were ground in an Alpine grinder. The prehydrolysate and the ground pulp material had an acidic pH of 1.46.

The prehydrolysate was first adjusted to pH 7.5 with a base, such as potassium hydroxide. Sodium citrate was added to the prehydrolysate at a 50 mmol concentration. Then, the prehydrolysate was sterilized in an autoclave at 121° C. for 20 minutes. If the pH changed after sodium citrate addition and sterilization, the pH was readjusted back to pH 7.5. To the pH 7.5 prehydrolysate, enzymes were added at 16 FPU cellulase/dry gram of pretreated solids, 20 U beta-glucosidase/dry gram of pretreated solids and 9 U xylanase/dry gram of pretreated solids. The prehydrolysate mixture containing the enzymes was transferred into a container with a spray nozzle.

The ground, pretreated pulp was sterilized in an autoclave at 121° C. for 20 minutes. The sterile pulp was laid on a strip of sterile aluminum foil 0.5 ft wide×1.0 ft long to simulate a small conveyor belt session. The pulp layer was evenly sprayed by the enzyme mixture prepared above in 100% prehydrolysate. The sprayed pulp was then transferred into a flask and incubated at 50° C. for enzymatic hydrolysis without any agitation. Two sprayed hydrolysis tests were carried out, one at 15% and the other at 20% pulp loading. After the spraying process, the sprayed pulp showed a pH of ~5.5 for the 15% pulp test and a pH of ~5.0 for the 20% pulp test. The test matrix is shown in Table 3, below.

TABLE 3

Spray hydrolysis matrix.

| Test No. | Pulp Load (Dry wt %) | Wet Pulp (g) | Prehydrolysate + Enzyme (ml) |
|---|---|---|---|
| 1 | 15 | 35.2 | 64.8 |
| 2 | 20 | 46.9 | 53.1 |

Within 24 hours, both tests showed complete liquefication of the biomass solids, and the total sugar titer and yield results are showed in Table 4. The yield was calculated in glucan conversion to glucose in the pretreated pulp materials. In both test cases at 48 hours, glucose yield was achieved at 97.0% and 87.0%, respectively for the 15% and 20% pulp loading.

TABLE 4

Spray hydrolysis yields on glucan.

| Test No. | Pulp Load (Dry wt %) | Glucose Yield (%) at 24 hr | Glucose Yield00 (%) at 48 hr |
|---|---|---|---|
| 1 | 15 | 82.9 | 97.0 |
| 2 | 20 | 80.0 | 87.0 |

Example 4

High Solids, Simultaneous Saccharification and Fermentation with *Saccharomyces cerevisiae* D5a (ATCC 200062)

High solids simultaneous saccharification and fermentation was tested on calcium bisulfite pretreated re-chipped chip biomass to demonstrate the effectiveness of the low level of inhibitors obtained. The calcium bisulfite pretreated softwood was ground in an Alpine grinder without any refining water or prehydrolysate as diluent. The calcium bisulfite pretreated softwood was also used without any water washes. The refined pulp was subsequently fermented using a simultaneous saccharification fermentation (SSF) method.

The frozen yeast stock (*Saccharomyces cerevisiae* D5a (ATCC 200062)) was first grown in a complex medium containing yeast extract 1% and peptone 2%, supplemented with 3% glucose. The stock seed culture was incubated in a shake flask on an orbital shaking incubator controlled at 38° C. and 200 rpm. The yeast seed culture was then centrifuged, and the yeast seed pellet was dissolved in a small volume of 100 mmol sodium citrate buffer. The yeast seed was inoculated at 2 g/L dry cell weight in the fermentation tests.

Figure 2:
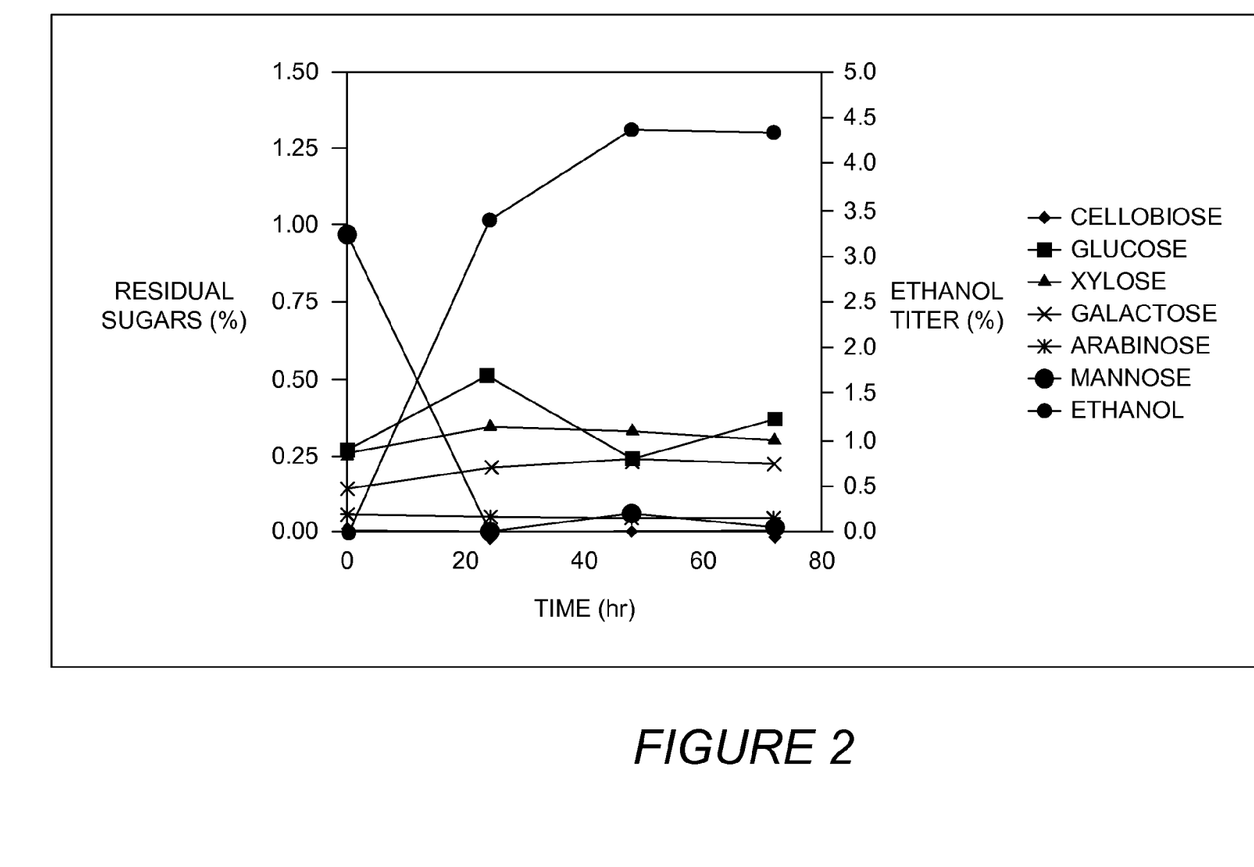

The fermentation was conducted in 50 ml volume in 125 ml Erlenmeyer shake flasks. Corn steep liquor was added at 4% as nutrients to the fermentation medium, supplemented with 0.11% urea. Pretreated pulp and prehydrolysate were sterilized separately in an autoclave at 121° C. for 20 minutes before fermentation. The SSF was initiated by combining the pretreated pulp (13.6%), prehydrolysate (undiluted), yeast seed (2 g/L), corn steep liquor (4%), cellulase (16 FPU/g pulp), beta-glucosidase (20 units/g pulp), and xylanase (9 U/g pulp). After all the ingredients were combined, the pulp materials were mixed using a stainless steel spatula, or a pipette, until the pulp materials and other materials were combined into a homogeneous, wet slurry. The pulp materials and the prehydrolysate occupied 80.4% of the total fermentation volume, and the remaining 19.6% volume included the enzymes, nutrients, and yeast seed. Fermentation in shake flasks was controlled at 38° C. and 150 rpm. Fermentation pH was controlled at ~pH 6.5 with a 50 mmol sodium citrate buffer (solid sodium citrate was added and pH was adjusted) by periodic pH testing and readjustment. The fermentation data is shown in FIG. 2. The ethanol production was complete in 48 hours, and an ethanol concentration of 4.4% was achieved. This represents 65.1% of the total sugars being converted to ethanol, or 66.6 gallons/standard ton of wood (or 1816 lbs of wood). The yeast used does not ferment xylose or arabinose, so the ethanol yield would be higher with a pentose-fermenting organism.

Example 5

High Solids, Simultaneous Saccharification and Fermentation with *Saccharomyces cerevisiae* T2

The *Saccharomyces cerevisiae* T2 was used in fermentation of calcium bisulfate pretreated re-chipped chips. The yeast seed was first grown in a complex medium containing yeast extract 1% and peptone 2%, supplemented with 3% glucose. The stock seed culture was incubated in a shake flask on an orbital shaking incubator controlled at 38° C. and 200 rpm. The yeast seed culture was then centrifuged and the yeast seed pellet was dissolved in a small volume of 100 mmol sodium citrate buffer. The yeast seed was inoculated at 2 g/L dry cell weight in the fermentation tests.

Figure 3:
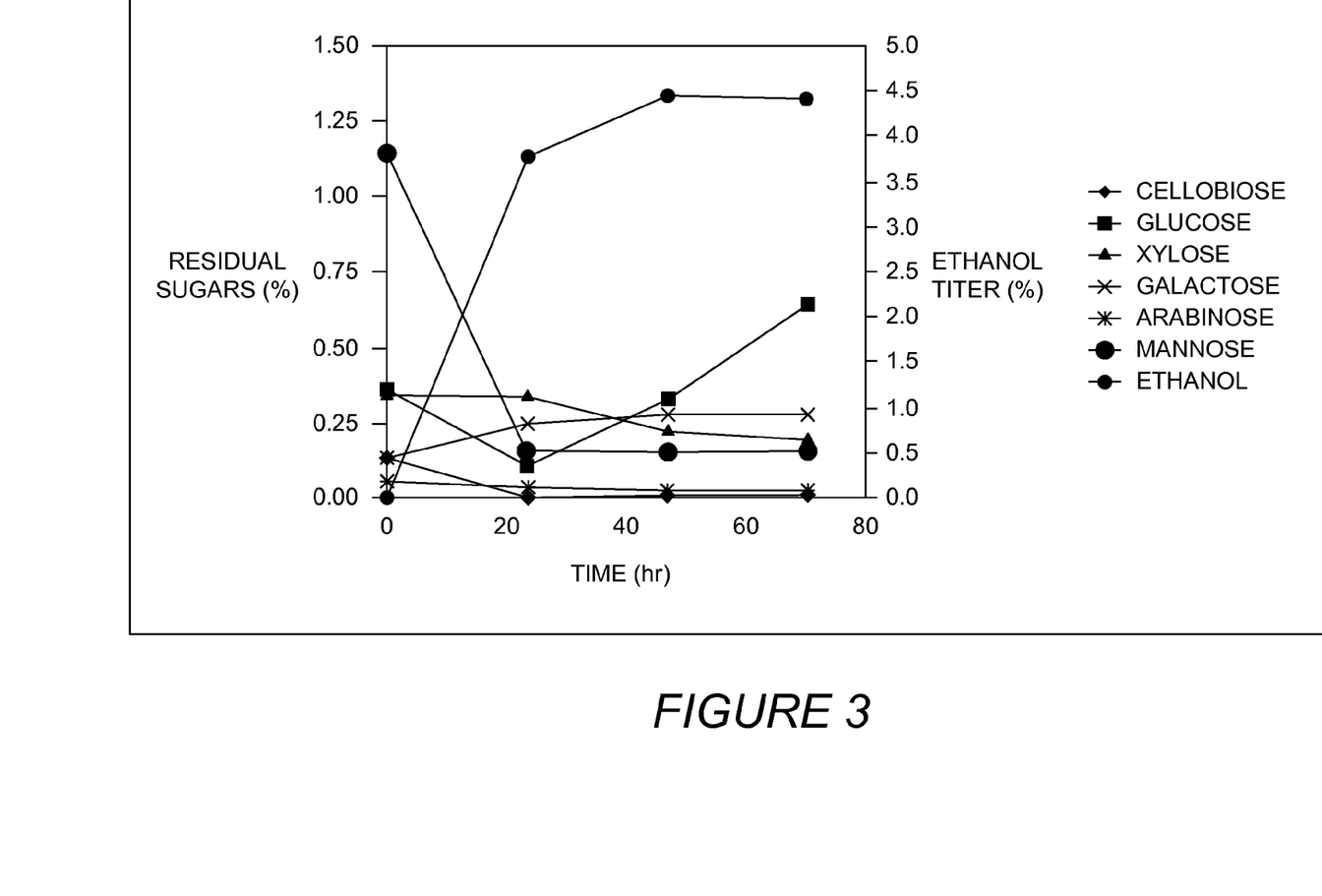

The fermentation was conducted in 50 ml volume in 125 ml Erlenmeyer shake flasks. Corn steep liquor was added at 4% as nutrients to the fermentation medium, supplemented with 0.11% urea. Pretreated pulp and prehydrolysate were sterilized separately in an autoclave at 121° C. for 20 minutes before fermentation. The SSF was initiated by adding the pretreated pulp (14.0%), liquor (full strength), yeast seed (2 g/L), corn steep liquor (4%), cellulase (16 FPU/g pulp), beta-glucosidase (20 units/g pulp), and xylanase (9 U/g pulp). After all the ingredients were added, the initial mixing was completed by a vigorous mixing using a stainless steel spatula, or a pipette, until all the pulp materials showed a homogeneous wet slurry. The total pulp materials and the prehydrolysate occupied 80.7% of the total fermentation volume and the rest 19.3% volume was from enzymes, nutrients, and yeast seed. Fermentation in shake flasks was controlled at 38° C. and 150 rpm. Fermentation pH was controlled at ~pH 6.5 by a 50 mmol sodium citrate buffer (solid sodium citrate was added and pH was adjusted) and by periodic pH checking and readjustment. The fermentation data is shown in FIG. 3. The ethanol production was complete in 48 hours, and an ethanol concentration of 4.4% was achieved. This represents 64.0% of the total sugars being converted to ethanol, or 65.3 gallons/standard ton of wood.

Example 6

Spray Application of Enzymes and Organisms in Prehydrolysate for High Solids Simultaneous Saccharification and Fermentation High solids simultaneous saccharification and fermentation was tested on calcium bisulfite pretreated re-chipped chip biomass using a high efficient enzyme and fermenting organism delivery method. In this method, the enzyme(s) and the fermenting organism delivery to pretreated biomass, the neutralization of the pretreated biomass, and the mixing were completed in one single spraying step. The pretreated biomass washing with water was not needed. Mechanical agitation for high solids and high viscosity mixing was unnecessary in the beginning of the high solids simultaneous saccharification and fermentation before its liquefaction.

The pretreated pulp materials were the same as in Example 3. The prehydrolysate was first adjusted to pH 7.5 with a base, such as potassium hydroxide. Sodium citrate was added to the prehydrolysate at a 50 mmol concentration. The prehydrolysate was sterilized in an autoclave at 121° C. for 20 minutes. The pH was readjusted back to pH 7.5 if there was a change. To the pH 7.5 prehydrolysate, SSF ingredients were added, including enzymes—cellulase (16 FPU/g pulp), beta-glucosidase (20 U/g pulp), xylanase (9 U/g pulp), corn steep liquor (4%), urea (0.11%), and yeast seed *Saccharomyces cerevisiae* T2 (2 g/L). The mixture of enzymes, yeast seed, nutrients and prehydrolysate was transferred into a container with a spray nozzle, to be used in the following sprayed SSF test.

The ground pretreated-pulp was sterilized in an autoclave at 121° C. for 20 minutes. The sterile pulp was laid on a strip of sterile aluminum foil 0.5 ft wide×1.0 ft long to simulate a small conveyor belt session. The pulp layer was evenly sprayed by the mixture of enzymes, yeast seed and nutrients prepared 100% prehydrolysate. The sprayed pulp was then transferred into a bottle and incubated at 38° C. for (SSF) ethanol fermentation without any agitation.

Three test sets were set up: one set for sprayed SSF, one set for mixed SSF and one set for top-addition non-well mixed SSF. The sprayed SSF was described above. After ingredients were added, the pre-mixed SSF was set up by a vigorous mixing using a stainless steel spatula or a pipette until all the pulp materials showed a homogeneous wet slurry. The top-addition non-well mixed SSF was set up by adding the pH 7.5 prehydrolysate, enzymes, yeast seed and nutrients to the pulp in the fermentation bottle without further mixing.

Figure 4:
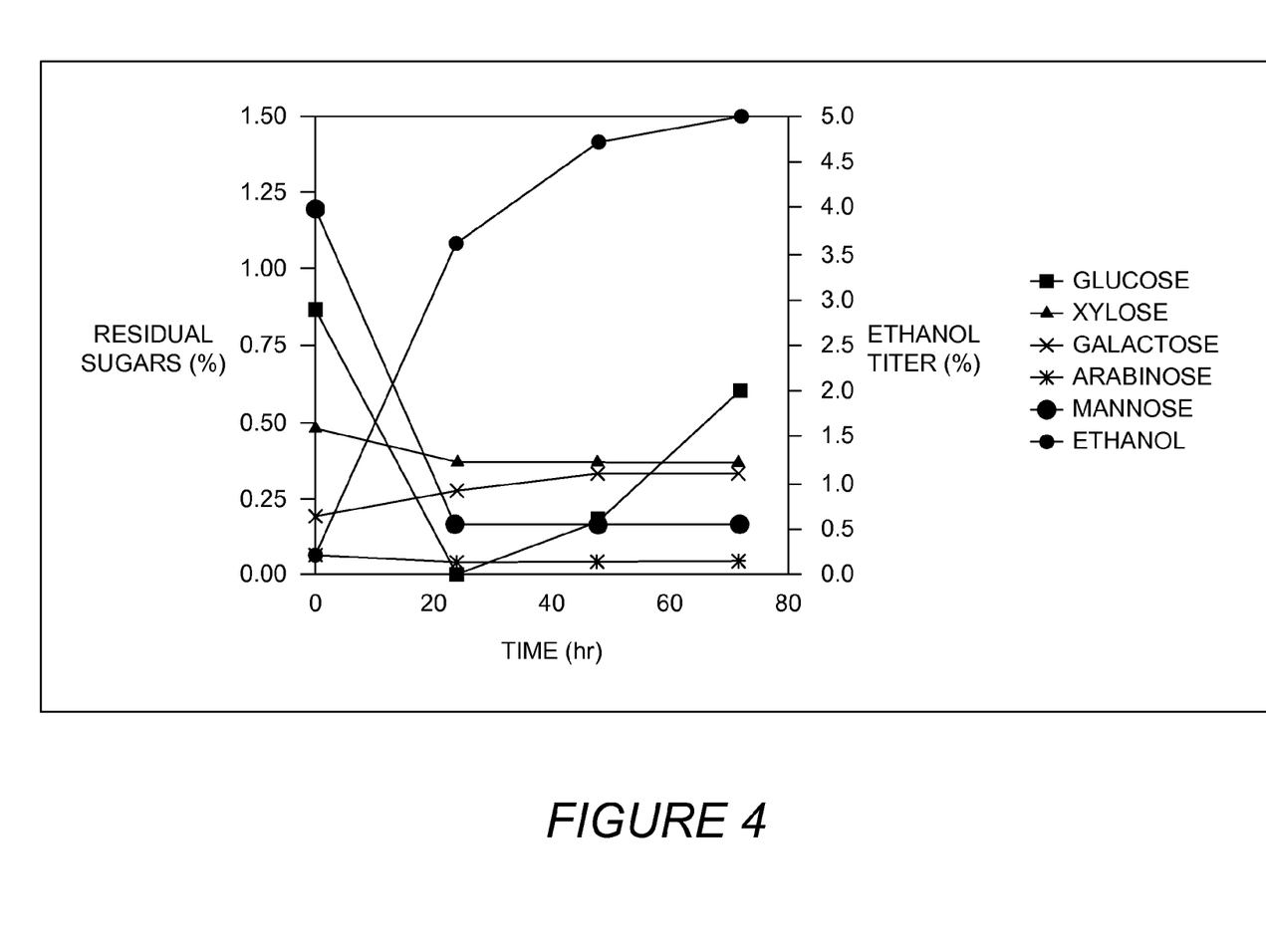

Ethanol titer and yield results are shown in the following Table 5. The sprayed SSF had almost identical ethanol titers and yields on the mixture of pretreated pulp and prehydrolysate as the pre-mixing SSF, indicating that the spraying delivery of enzymes, yeast seed and nutrients prepared in 100% prehydrolysate was effective. One single step of spraying could accomplish mixing as well as pulp neutralization to the appropriate simultaneous enzymatic hydrolysis and fermentation pH or SSF pH (FIG. 4). This was accomplished without a mechanical mixing step by an impeller. The control non-mixing SSF showed poor ethanol fermentation titer and yields.

TABLE 5

Ethanol yields of simultaneous saccharification and fermentation yields on 14.9% pulp using spray delivery or pre-mixing of the enzymes and organisms.

| Test No. | Mixing Method | Max Ethanol Titer (%) | Ethanol Yield (%) on Sugar | Ethanol Yield (gal/standard ton) |
| --- | --- | --- | --- | --- |
| 1 | Spray | 4.79 | 65.0 | 66.4 |
| 2 | Spray | 4.83 | 65.5 | 66.9 |
| 3 | Pre-mixing | 4.83 | 65.5 | 66.9 |
| 4 | Pre-mixing | 4.88 | 66.2 | 67.6 |
| 5 | No mixing | 0.92 | 12.5 | 12.7 |
| 6 | No mixing | 1.01 | 13.7 | 14.0 |

Example 7

Figure 5:
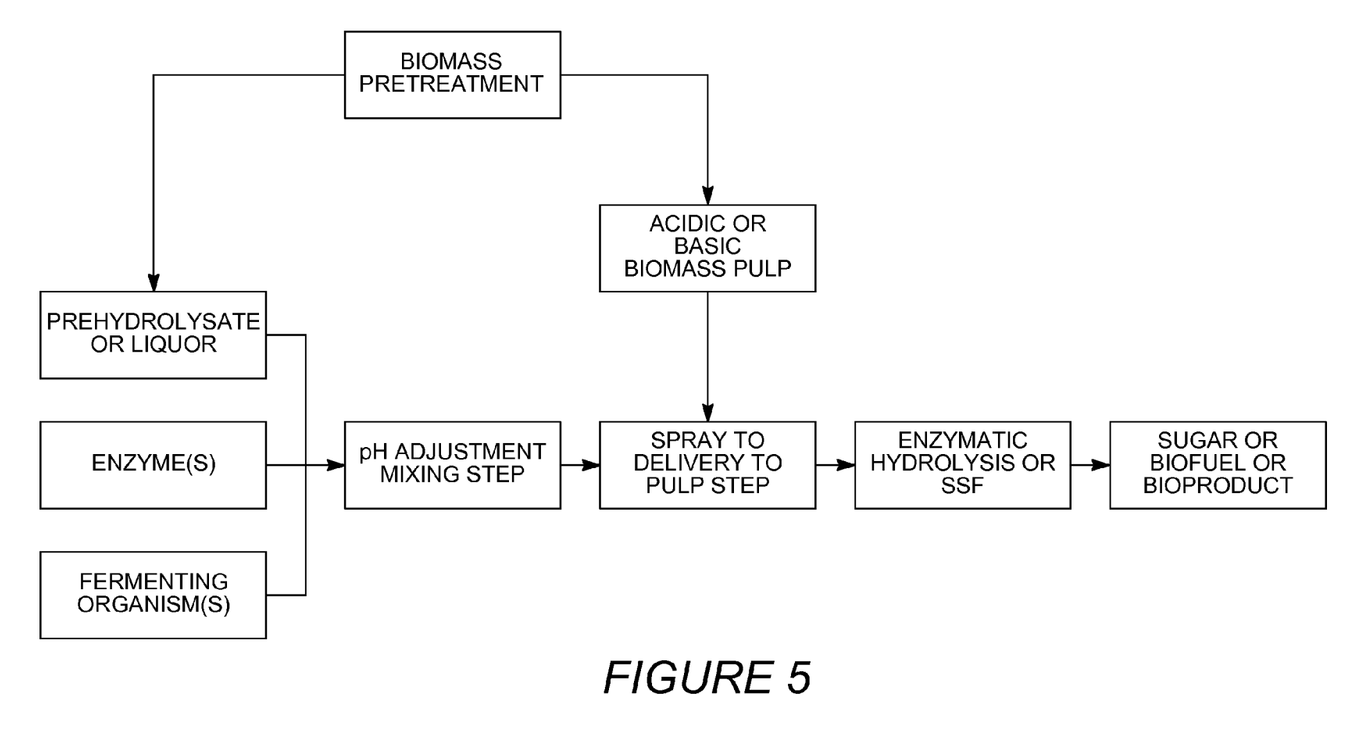

Process Flow Diagram of Spraying Enzyme(s), Fermenting Organism(s), and Nutrients in a Prehydrolysate Diluent onto Pretreated Biomass Solids The process flow diagram shown in FIG. 5 summarizes the integration of an effective spraying delivery of fermenting organism and/or enzymes and nutrients dissolved in a prehydrolysate diluent to an acidic or basic pretreated pulp material to achieve a proper final pH for either enzymatic hydrolysis and/or simultaneous saccharification fermentation.

Example 8

Figure 6:
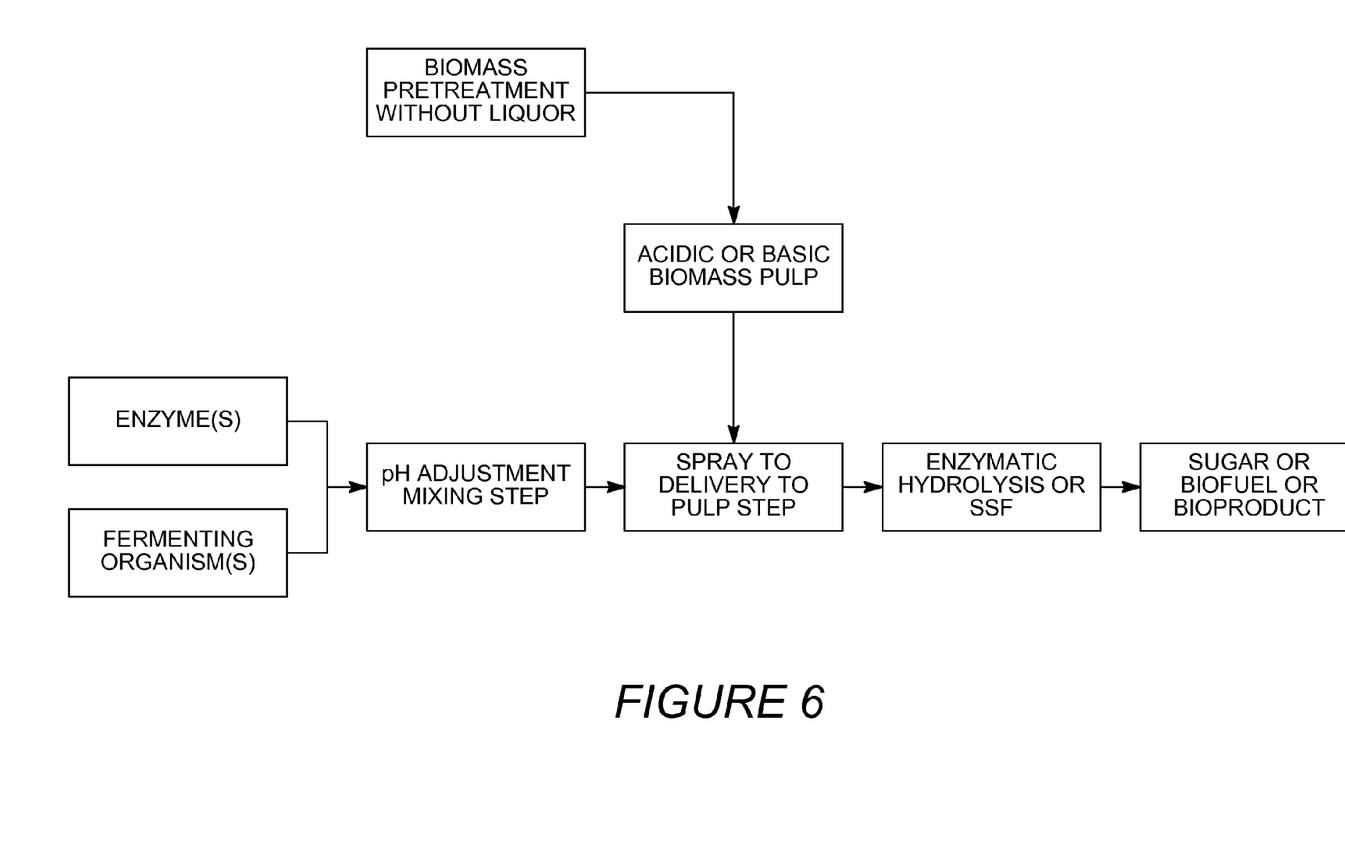

Process Flow Diagram of Spraying Enzyme(s), Fermenting Organism(s), and Nutrients without a Prehydrolysate Diluent onto Biomass Solids The process flow diagram shown in FIG. 6 summarizes the integration of an effective spraying delivery of fermenting organism and/or enzymes and nutrients without a prehydrolysate diluent to an acidic or basic pretreated pulp material to achieve a proper final pH for either enzymatic hydrolysis and/or simultaneous saccharification fermentation.

Example 9

Figure 7:
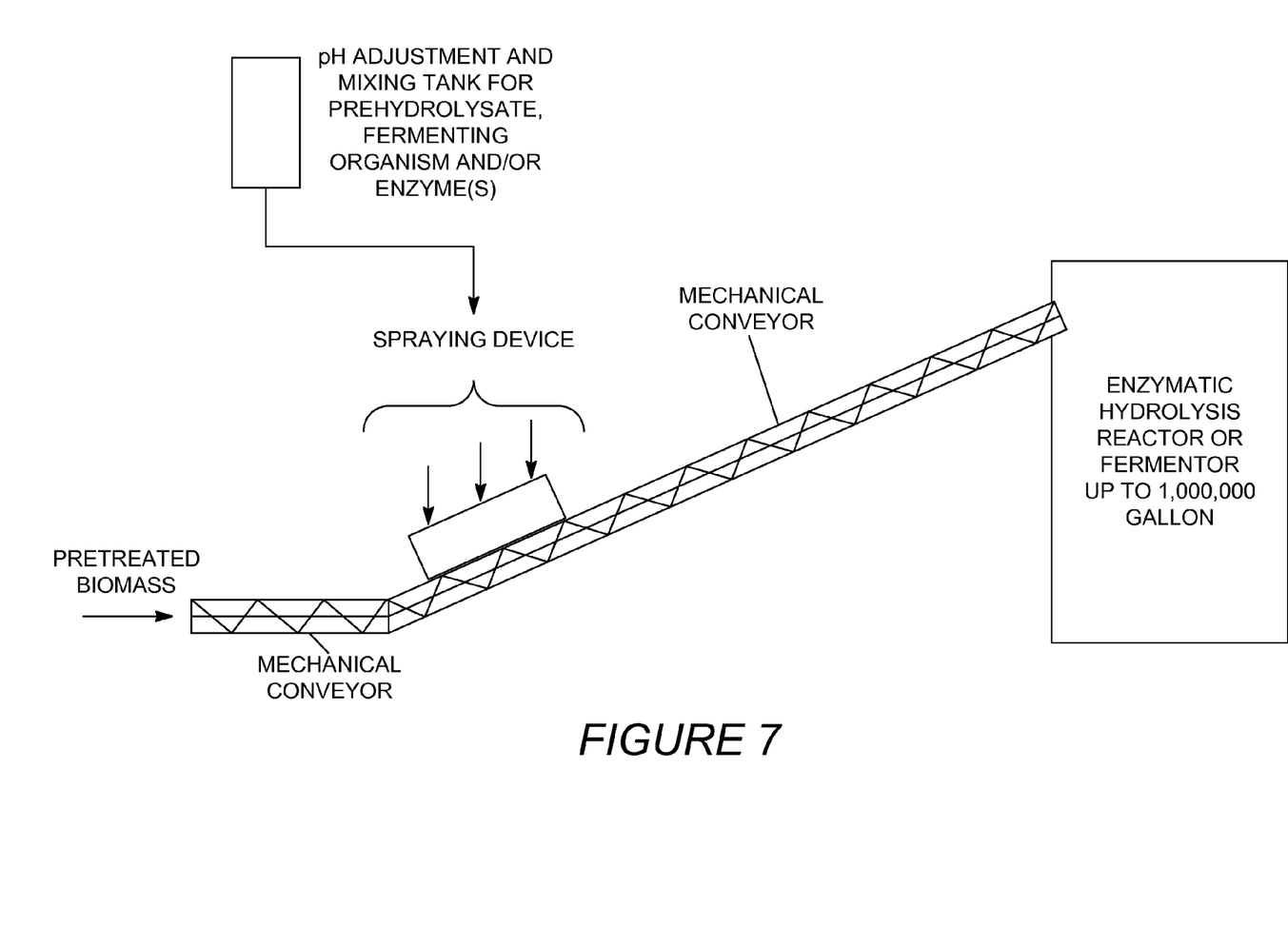

Process Design for Spraying Enzymes, Fermentation Organisms, and/or Nutrients onto Biomass Solids Using a Conveyor to Transport the Biomass Solids Under the Spraying Apparatus and into a Reactor This process design shown in FIG. 7 utilizes spraying to deliver a mixture of prehydrolysate, fermenting organism(s) and/or enzyme(s) is simple in structure, less in capital cost, low in maintenance, and effective to evenly distribute enzymes, nutrients, and fermenting cells to pretreated fibers or pulp materials. Enzymatic hydrolysis ingredients or fermentation ingredients can be delivered in one single step to accomplish both mixing and pretreated material neutralization.

Although the methods described herein have been described in connection with some variations, it is not intended to be limited to the specific form set forth herein. Rather, the scope of the methods described herein is limited only by the claims. Additionally, although a feature may appear to be described in connection with particular variations, one skilled in the art would recognize that various features of the described variations may be combined in accordance with the methods described herein.

Enumerated Embodiments

The following enumerated embodiments are representative of some aspects of the invention.

1. A method of producing a saccharification product from a pretreated biomass composition, the method comprising:
    a) spraying a liquid comprising one or more saccharification enzymes onto the pretreated biomass composition to form an impregnated biomass composition; and
    b) maintaining the impregnated biomass composition under suitable conditions to promote hydrolysis of components in the impregnated biomass composition to produce the saccharification product.

2. The method of embodiment 1, wherein the liquid further comprises one or more fermentation organisms, and wherein the one or more fermentation organisms ferment sugars produced by hydrolysis to produce a fermentation product.

3. A method of producing a saccharification product from a pretreated biomass composition comprising a prehydrolysate and pretreated biomass solids, the method comprising:
   a) separating the prehydrolysate from the pretreated biomass solids to form a first prehydrolysate liquid;
   b) adding one or more saccharification enzymes to the first prehydrolysate liquid to form a second prehydrolysate liquid;
   c) spraying the second prehydrolysate liquid onto the pretreated biomass solids to form an impregnated biomass composition; and
   d) maintaining the impregnated biomass composition under suitable conditions to promote enzymatic hydrolysis of the impregnated biomass composition to produce the saccharification product.

4. The method of embodiment 3, wherein the method further comprises:
   a) adding one or more fermentation organisms to the saccharification product; and
   b) maintaining the saccharification product under suitable conditions to promote fermentation of sugars produced by hydrolysis to produce a fermentation product.

5. The method of either of embodiments 3 or 4, wherein the pretreated biomass solids are not rinsed or conditioned before spraying with the second prehydrolysate.

6. The method of any of embodiments 3-5, further comprising adjusting the pH of the first or second prehydrolysate liquid to a pH range of 3.0 to 9.0 prior to the spraying step.

7. The method of any of embodiments 1-6, wherein the one or more saccharification enzymes are selected from the group consisting of cellulase, beta-glucosidase, xylanase, other hemicellulases, and mixtures thereof.

8. The method of any of embodiments 2, 4-7, wherein the fermentation organisms are selected from the group consisting of yeast, mold, algae, bacteria, and mixtures thereof.

9. The method of any of embodiments 3-8, further comprising mixing the pretreated biomass composition with the second prehydrolysate liquid.

10. The method of any of embodiments 1-9, wherein the pretreated biomass solids are transported on a screw or a belt conveyer during the spraying step to form the impregnated biomass composition.

11. The method of any of embodiments 1-10, further comprising moving the impregnated biomass composition with a belt or screw conveyer into a reactor prior to hydrolysis, fermentation, or hydrolysis and fermentation.

12. The method of embodiment 11, further comprising circulating the impregnated biomass composition inside the reactor.

13. The method of embodiment 12, wherein a slurry pump, a slow agitator, or a slow impeller circulates the impregnated biomass composition.

14. The method of any of embodiments 3-13, wherein the pretreated biomass composition comprises wood chips, and wherein the wood chips are size reduced prior to pretreatment, such that prior to size reduction, 50-100% of the wood chips pass through a +7 mm round hole screen, and after size reduction, 50-100% of the wood chips pass through a +3 mm round hole screen.

15. The method of any of embodiments 3-14, wherein the pretreated biomass solids are ground up prior to spraying with the second prehydrolysate liquid.

16. The method of any of embodiments 3-15, wherein the pretreated biomass composition is produced from an acid sulfite or acid bisulfite pretreatment process.

17. The method of any of embodiments 3-15, wherein the pretreated biomass composition is produced from an alkaline sulfite or alkaline bisulfite pretreatment process.

18. The method of any of embodiments 3-15, wherein the pretreated biomass composition is produced from a neutral chemical pretreatment process or a pretreatment process using water and no additional chemicals.

19. The method of any of embodiments 3-18, wherein the fermentation product has a titer greater than 4.0%.

20. The method of any of embodiments 3-19, wherein the hydrolysis produces a sugar yield of 80-100% of the pretreated biomass composition.

21. The method of any of embodiments 3-20, wherein the fermentation converts 60-100% of sugars to the fermentation product.

22. A method of producing a fermentation product from a pretreated biomass composition comprising a prehydrolysate and pretreated biomass solids, the method comprising:
   a) separating the prehydrolysate from the pretreated biomass solids to form a first prehydrolysate liquid;
   b) adding one or more saccharification enzymes and one or more fermentation organisms to the first prehydrolysate liquid to form a second prehydrolysate liquid;
   c) spraying the second prehydrolysate liquid onto the pretreated biomass solids to form an impregnated biomass composition; and
   d) maintaining the impregnated biomass composition under suitable conditions to promote enzymatic hydrolysis of the impregnated biomass composition and fermentation of the saccharification product to form the fermentation product.

23. The method of either embodiment 1 or 2, wherein the liquid is a prehydrolysate produced from the pretreated biomass composition.

24. The method of either embodiment 1 or 2, wherein the liquid is a prehydrolysate produced from a second pretreated biomass composition.

Although individual features of the methods described herein may be included in different claims, these may be advantageously combined, and the inclusion in different claims does not imply that a combination of features is not feasible and/or advantageous. Also, the inclusion of a feature in one category of claims does not imply a limitation to this category, but rather the feature may be equally applicable to other claim categories, as appropriate. Where a composition or process 'comprises' one or more specified items or steps, others can also be included. The invention also contemplates, however, that the described composition or process may be used without other items or steps and thus it includes the recited composition or process 'consisting of' or 'consisting essentially of' the recited items, materials or steps, as those terms are commonly understood in patent law.

Terms and phrases used in this document, and variations thereof, unless otherwise expressly stated, should be construed as open ended as opposed to limiting. As examples of the foregoing: the term "including" should be read to mean "including, without limitation" or the like; the terms "example" or "some variations" are used to provide exemplary instances of the item in discussion, not an exhaustive or limiting list thereof; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of methods and compositions described herein may be described or claimed in the singular, the plural is contemplated to be within the scope thereof unless limitation to the singular is explicitly stated. The presence of broadening words and phrases such as "one or more," "at least," "but not limited to," "in some variations," "in some non-limiting variations" or other like phrases in some instances shall not be read to mean that the narrower case is intended or required in instances where such broadening phrases may be absent.

We claim:

1. A method of producing a saccharification product from a pretreated biomass composition comprising a prehydrolysate and pretreated biomass solids, the method comprising:
   a) separating the prehydrolysate from the pretreated biomass solids to form a first prehydrolysate liquid;
   b) adding one or more saccharification enzymes to the first prehydrolysate liquid to form a second prehydrolysate liquid, under suitable conditions to promote subsequent enzymatic hydrolysis;
   c) spraying the second prehydrolysate liquid onto the pretreated biomass solids to form an impregnated biomass composition; and
   d) maintaining the impregnated biomass composition under suitable conditions to promote enzymatic hydrolysis of the impregnated biomass to produce the saccharification product.

2. The method of claim 1, wherein the method further comprises after step d):
   e) adding one or more fermentation organisms to the saccharification product; and
   f) maintaining the saccharification product under suitable conditions to promote fermentation of sugars produced by hydrolysis to produce a fermentation product.

3. The method of claim 1, wherein the pretreated biomass solids are not rinsed or conditioned before spraying with the second prehydrolysate.

4. The method of claim 1, further comprising adjusting the pH of the first or second prehydrolysate to a pH range of 3.0 to 9.0 prior to the spraying step.

5. The method of claim 1, wherein the one or more saccharification enzymes are selected from the group consisting of cellulose, beta-glucosidase, xylanase, other hemicellulases, and mixtures thereof.

6. The method of claim 2, wherein the one or more fermentation organisms are selected from the group consisting of yeast, mold, algae, bacteria, and mixtures thereof.

7. The method of claim 1, further comprising mixing the pretreated biomass composition with the second prehydrolysate liquid.

8. The method of claim 1, wherein the pretreated biomass solids are transported on a screw or a belt conveyer during the spraying step to form the impregnated biomass composition.

9. The method of claim 1, further comprising moving the impregnated biomass composition with a belt or screw conveyer into a reactor for the hydrolysis.

10. The method of claim 1, wherein the pretreated biomass composition comprises wood chips, and wherein the wood chips are size reduced prior to pretreatment, such that prior to size reduction 50-100% of the wood chips pass through a +7 mm round hole screen, and after size reduction, 50-100% of the wood chips pass through a +3 mm round hole screen.

11. The method of claim 1, wherein the pretreated biomass solids are ground up prior to spraying with the second prehydrolysate liquid.

12. The method of claim 1, wherein the pretreated biomass composition is produced from an acid sulfite or acid bisulfite pretreatment process.

13. The method of claim 1, wherein the pretreated biomass composition is produced from an alkaline sulfite or alkaline bisulfite pretreatment process.

14. The method of claim 1, wherein the pretreated biomass composition is produced from a neutral chemical pretreatment process or a pretreatment process using water and no additional chemicals.

15. The method of claim 2, wherein the fermentation product has a titer greater than 4.0%.

16. The method of claim 1, wherein the hydrolysis produces a sugar yield of 80-100% of the pretreated biomass composition.

17. The method of claim 2, wherein the fermentation converts 60-100% of the sugars to the fermentation product.

18. A method of producing a fermentation product from a pretreated biomass composition comprising a prehydrolysate and pretreated biomass solids, the method comprising:
   a) separating the prehydrolysate from the pretreated biomass solids to form a first prehydrolysate liquid;
   b) adding one or more saccharification enzymes and one or more fermentation organisms to the first prehydrolysate liquid to form a second prehydrolysate liquid, under suitable conditions to promote subsequent enzymatic hydrolysis;
   c) spraying the second prehydrolysate liquid onto the pretreated biomass solids to form an impregnated biomass composition; and
   d) maintaining the impregnated biomass composition under suitable conditions to promote enzymatic hydrolysis of the impregnated biomass composition to form a saccharification product and fermentation of the saccharification product to form the fermentation product.

* * * * *